United States Patent [19]
Pletka et al.

[11] Patent Number: 5,622,430
[45] Date of Patent: Apr. 22, 1997

[54] METHOD OF TESTING THE HEAT INSULATION ACTION OF BODIES ESPECIALLY OF HEAT INSULATION BODIES

[75] Inventors: Hans D. Pletka, Freigericht; Ulrich Reichau, Mainaschaff; Michael Schmidt, Hanau, all of Germany

[73] Assignee: Degussa Aktiengesellschaft, Frankfurt, Germany

[21] Appl. No.: 404,089

[22] Filed: Mar. 14, 1995

Related U.S. Application Data

[63] Continuation-in-part of Ser. No. 334,341, Nov. 2, 1994, abandoned.

[30] Foreign Application Priority Data

Nov. 5, 1993 [DE] Germany .......................... 43 37 840.4

[51] Int. Cl.⁶ .......................... G01N 25/00; G01N 25/18
[52] U.S. Cl. ................................. 374/45; 374/44
[58] Field of Search .................... 374/45, 44, 43

[56] References Cited

U.S. PATENT DOCUMENTS

| | | | |
|---|---|---|---|
| 4,246,785 | 1/1981 | Sellers et al. ............... | 374/43 |
| 4,630,938 | 12/1986 | Piorkowska et al. ......... | 374/44 |
| 5,248,198 | 9/1993 | Droege ......................... | 374/43 |

FOREIGN PATENT DOCUMENTS

| | | | |
|---|---|---|---|
| 0089760 | 9/1983 | European Pat. Off. . | |
| 0214203 | 10/1984 | Germany ................... | 374/44 |
| 0225875 | 8/1985 | Germany ................... | 374/44 |
| 3820862 | 12/1989 | Germany . | |
| 0058242 | 3/1988 | Japan ......................... | 374/44 |
| 2012875 | 5/1994 | Russian Federation ... | 374/44 |
| 0920489 | 4/1982 | U.S.S.R. .................... | 374/44 |
| 1276972 | 12/1986 | U.S.S.R. .................... | 374/44 |
| 1303920 | 4/1987 | U.S.S.R. .................... | 374/44 |
| 1330527 | 8/1987 | U.S.S.R. .................... | 374/44 |
| 1658053 | 6/1991 | U.S.S.R. .................... | 374/44 |
| 1711052 | 2/1992 | U.S.S.R. .................... | 374/44 |
| 1721491 | 3/1992 | U.S.S.R. .................... | 374/44 |
| 8606164 | 10/1986 | WIPO ......................... | 374/44 |

OTHER PUBLICATIONS

Vlasov, V. et al., "Automatic Determination of the Thermal Diffusivity of Heat Insulators," J. Eng. Physics, vol. 11, No. 3 (Sep. 1966).

Taylor, R., "Construction of Apparatus for Heat Pulse Thermal Diffusivity Measurements from 300–3000K," J. Phys. E: Sci. Instrum., vol. 13, No. 11 (Nov. 1980).

Primary Examiner—Diego F. F. Gutierrez
Attorney, Agent, or Firm—Beveridge, DeGrandi, Weilacher & Young, L.L.P.

[57] ABSTRACT

A method of testing heat insulation shaped bodies for purposes of evaluation wherein a shaped heat insulation body is placed in a measuring space where the initial temperature of the heat insulation body is measured under ambient conditions prior to heating. The shaped heat insulation body is then subjected to thermal radiation for contactless heating for a sufficient period of time to heat the body to an elevated temperature. Then the radiation is removed and the initial temperature decrease of the body is measured with contactless temperature measurement to obtain a temperature/time profile. The thermal conduction coefficient |k| is calculated as follows:

$$|k| = \frac{1}{t} \ln \frac{\theta(t) - \theta_u}{\theta_o}$$

and compared with a standard thermal conduction coefficient, wherein (t) is time, $\theta_o$ is the temperature the surface of said body after heating, $\theta_u$ is the temperature of the surroundings, and $\theta(t)$ is the surface temperature at the time (t).

1 Claim, 5 Drawing Sheets

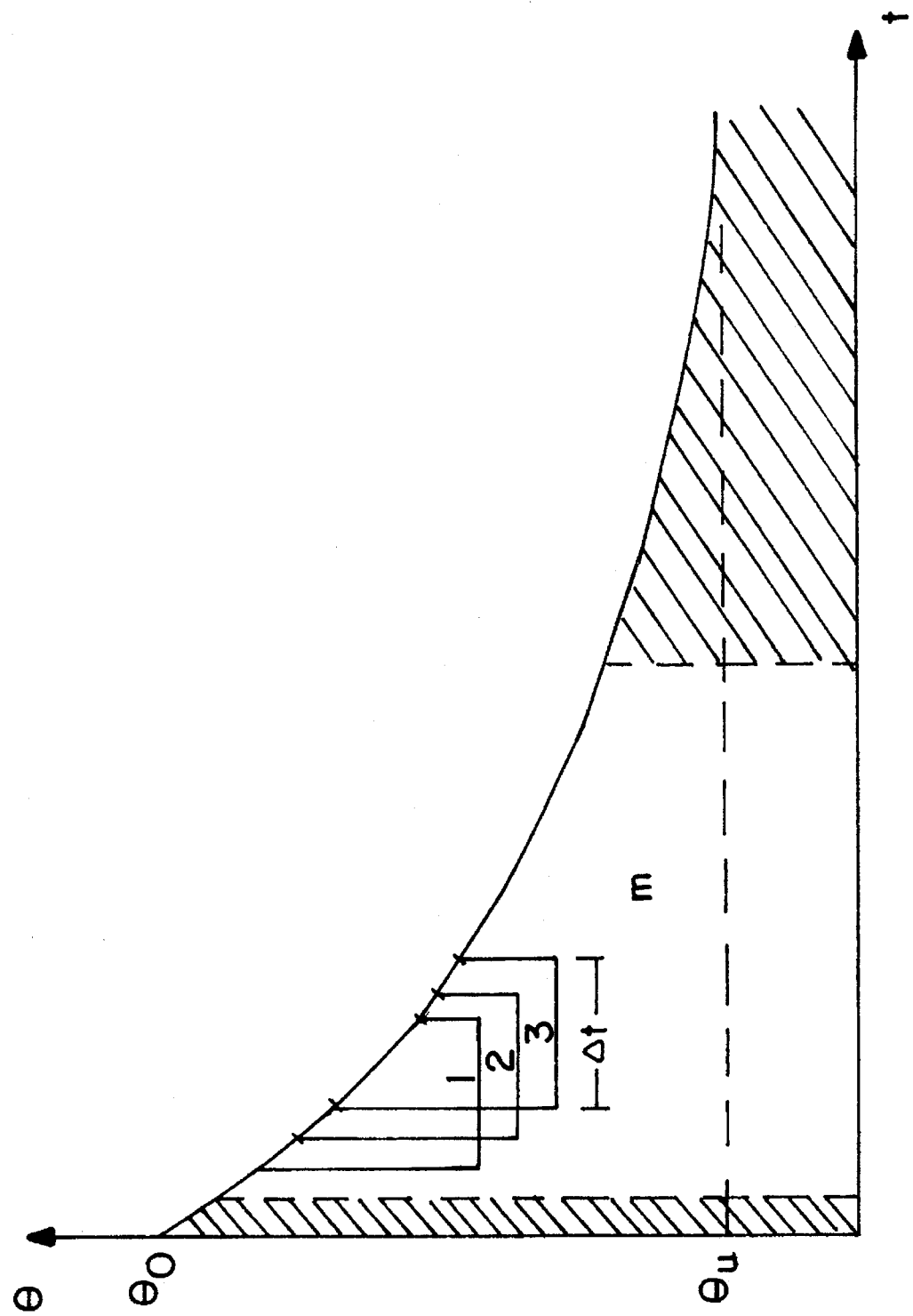

METHOD OF TESTING THE HEAT INSULATION ACTION OF BODIES ESPECIALLY OF HEAT INSULATION BODIES

REFERENCE TO THE RELATED APPLICATION

This is a continuation-in-part of application Ser. No. 08/334,341 filed Nov. 2, 1994, now abandoned which is relied on herein.

INTRODUCTION AND BACKGROUND

The present invention relates to a method of testing the heat insulation action of bodies, especially of heat insulation products.

Heat insulation products, especially evacuated heat insulation bodies, are ideal insulating materials for refrigerating devices. They are formed of a gas-tight casing which contains e.g. a precipitated silica (such as FK 500 LS of Degussa AG) as the filler. The entire heat insulation body is evacuated to a defined internal pressure in order to raise the insulating action. The precipitated silica contained as filler in order to assure a good insulating action over a long time period exhibits a defined water content (EP-B 0,396,696). Such heat insulation bodies are produced, for example, by a process of:

a) preparing a finely distributed, powdery or fibrous material exhibiting a water absorption capacity of 4 to 50% by weight (at 23° C. and 85% relative moisture) and optionally drying it under conditions sufficient for the expelling of the surface water, b) optionally pressing the powdery or fibrous material, c) placing the optionally dried and optionally pressed powdery or fibrous material in a casing which comprises an opening for evacuation and exhibits a water-vapor permeability of 0.1 to 0.5 g/(m²·d) (at 23° C. and 85% relative moisture) and gas permeabilities of 0.1 to 0.5 cm³/(m²·d·bar) (at 23° C.), d) evacuating the casing and e) closing the evacuation opening of the casing with retention of the vacuum in the interior of the casing (EP-B 0,396,961).

The large-scale production of a rather large number of these heat insulation formed bodies has the problem of a economical and non-destructive quality control which can furnish reliable information about the quality of the heat insulation of the individual heat insulation body produced in the manufacturing operation.

It is known that the heat insulation action of evacuated heat insulation bodies can be determined by placing the heat insulation body into an evacuated chamber and investigating it there. The known method has the disadvantage that it is too troublesome and expensive for large-scale industrial use (D. Buettner et al. High Temp.—High Pressures, 15 (2), 233–40 (1983)).

Tests of heat insulation bodies show the influence of the internal pressure and of the relative moisture on the thermal conductivity coefficient; $\lambda$. The thermal conductivity coefficient of a material is determined in a state of stationary heat flow after more than 12 hours dwell time and at a temperature gradient of 20° C. to −20° C. across the heat flow. Typical measuring times must be approximately 2 to 3 hours below stationary temperature conditions (constant heat flow in the heat insulation formed body) for heat insulation formed bodies. This amount of time is too great for a quality control program parallel to large-scale manufacture.

SUMMARY OF THE INVENTION

An object of the invention is to overcome the problem in the art of testing the heat insulation action of bodies, especially of heat insulation bodies. In achieving the above and other objections, one feature of the invention resides in a method wherein thermal relaxation behavior is determined on the heat insulation bodies, by means of contactless temperature measuring.

In accordance with the invention, there is disclosed a method of testing heat insulation shaped bodies for purposes of evaluation including placing a shaped heat insulation body such as a panel, sheet or other typical form of heat insulation body having a surface in a measuring space defining a location. The initial temperature of the heat insulation body is then measured under ambient conditions prior to heating. This measurement information is then typically stored in suitable form such as memory means. Then the shaped heat insulation body is subjected to exposure to thermal radiation for contactless heating of the surface of the body facing the source of thermal radiation which is generally located some distance from the surface of the body so as to provide for contactless heating. The heating is carried out with a sufficient amount of heat for a sufficient period of time to heat at least the exposed surface of the heat insulation body to an elevated temperature above ambient temperature.

The source of the radiation is then moved so as to no longer heat the surface. The temperature decrease of the surface by free air convection is then measured with contactless temperature measurement means to obtain a temperature/time profile of the surface. Then the coefficient |k| for the insulation is calculated as follows by using two points of the temperature/time profile:

$$|k| = \frac{1}{t} \cdot \ln \frac{\theta(t) - \theta_u}{\theta_o}$$

wherein (t) is time, $\theta_o$ is the temperature of the surface of the body after heating up, $\theta_u$ is the temperature of the surroundings, and $\theta(t)$ is the surface temperature at time (t). Then, the calculated |k| value and $\theta_o$ is compared with a standard and a determination is made as to whether the body subjected to the test meets the required standard established from the desired insulation product. In this way the cooling off constant |k| can be compared with a previuosly determined standard |k| value for an acceptable heat insulation product. Then if the tested product has a |k| value above or below the standard, a judgement can be made to reject or accept the product in a rapid way. In this way good quality control can be achieved in the manufacturing plant.

BRIEF DESCRIPTION OF DRAWINGS

The present invention will be further understood with reference to the drawings, wherein:

FIG. 5 is a plot of calculated cooling off curve.

DETAILED DESCRIPTION OF INVENTION

Figure 1:
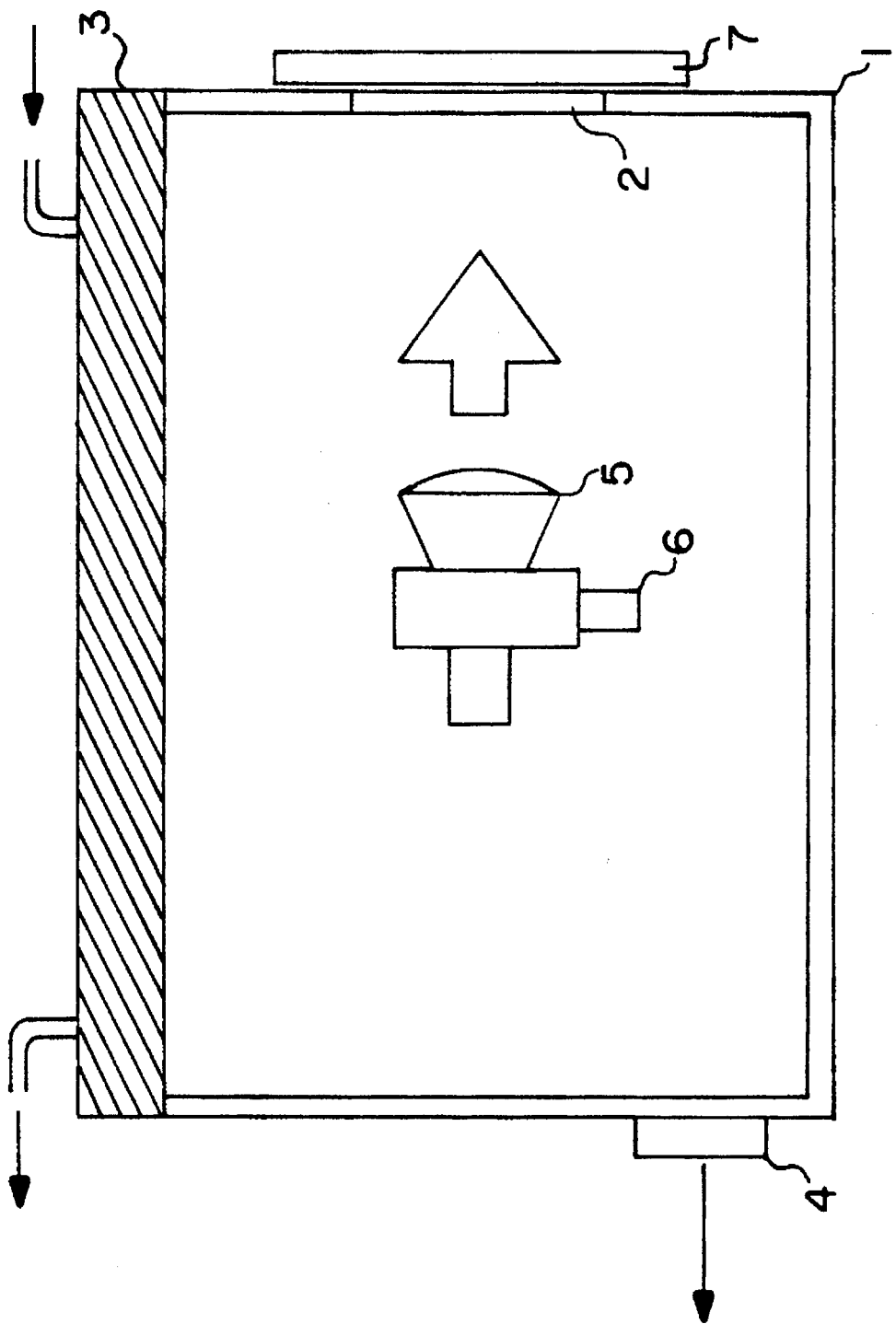
FIG. 1 is a schematic cross-section of an apparatus suitable for carrying out the present invention.

In carrying out the present invention, the test method is based on the following physical considerations in which the formula symbols have the following meanings:

| | | |
|---|---|---|
| A | Surface Area | $m^2$ |
| b | Thermal penetration number | $J \cdot m^{-2} \cdot K^{-1} \cdot s^{-\frac{1}{2}}$ |
| a | Thermal diffusivity | $m^2 \cdot s^{-1}$ |
| c | Specific heat capacity | $J \cdot kg^{-1} \cdot K^{-1}$ |
| λ | Thermal conductivity coefficient | $W \cdot m^{-1} \cdot K^{-1}$ |
| ρ | Density | $kg \cdot m^{-3}$ |
| t | Time | s |
| x | Position [locus] | m |
| Q̇ | Heat Flux | W |
| Q | Amount of heat | J |
| θ | Temperature | °C. |

Superscripts and subscripts

| | |
|---|---|
| o | Surface |
| u | Environment |

The differential equation of thermal conductivity in the one-dimensional case for Cartesian coordinates is:

$$\frac{\delta \theta}{\delta t} = \frac{\lambda}{\rho \cdot c} \cdot \frac{\delta^2 \theta}{\delta x^2} \quad (1)$$

with $$a = \frac{\lambda}{\rho \cdot c}$$

The foregoing equations describe the behavior of temperature fields variable in time without inner heat sources.

For the model of the unilaterally "infinitely" expanded body the particular solution of the equation follows in the simple case of the surface temperature constantly maintained high in order to heat the body:

$$\theta = \Delta\theta_o \frac{2}{\sqrt{\pi}} \cdot \int_{n=0}^{n=\frac{x}{\sqrt{4at}}} e^{-n^2} \delta n \quad (2)$$

with the magnitude Δθhd o= Surface temperature minus inner temperature

The solution of the equation for the temperature field in the body is obtained via an analogous extrapolation with the Gaussian probability integral.

There follows the calculation of the heat flow through the surface with the condition:

$$\frac{\delta Q}{\delta t} = -\lambda \left. \frac{\delta \theta}{\delta x} \right|_{x=0} \delta A \quad (3)$$

with $$\frac{\delta \theta}{\delta x} = \Delta\theta_o \cdot \frac{2}{\sqrt{4\pi at}} e^{-\frac{x^2}{4at}} \quad (4)$$

From the above, it follows that for the surface, x=0:

$$\frac{\delta Q}{\delta t} = \sqrt{\frac{\lambda \rho c}{\pi t}} \cdot \Delta\theta_o \cdot A \quad (5)$$

Integration of the expression over the time period of heating yields the amount of heat supplied to the body; to wit:

$$Q = \frac{2}{\sqrt{\pi}} \sqrt{\lambda \rho c} \, \Delta\theta_o A \sqrt{t} \quad (6)$$

The calculation of the heat flow density and of the amount of heat stored in a heat insulation body at a 30° C. temperature difference between surface and center of formed body can take place, for example, as follows using the following given values which are typical for heat insulation panels:

$\lambda_1 = 0.007 W \cdot m^{-1} \cdot K^{-1} \rho = 180 \, kg \cdot m^{-3}; \, c = 1200 \, J \cdot kg^{-1} \cdot k^{-1}; \, \Delta\theta_o = 30°$ C.

The heat penetration number follows from the above values $$b_1 = \sqrt{\lambda \rho c} = 38.88 \, J \cdot m^{-2} \cdot K^{-1} \cdot s^{1/2}$$

and with $\lambda_2 = 0.020 \, W \cdot m^{-1} \cdot K^{-1}$ the heat penetration number $b_2 = 65.72 \, J \cdot m^{-2} \cdot K^{-1} \cdot s^{1/2}$ The results of the calculation are cited in the following table:

| Time Seconds | Heat flow density 1 $W \cdot m^{-2}$ | Heat flow density 2 $W \cdot m^{-2}$ | Heat amount 1 $J \cdot m^{-2}$ | Heat amount 2 $J \cdot m^{-2}$ |
|---|---|---|---|---|
| 1 | 658 | 1112 | 1316 | 2225 |
| 5 | 294 | 497 | 2943 | 4975 |
| 10 | 208 | 352 | 4162 | 7035 |
| 20 | 147 | 249 | 5886 | 9949 |
| 30 | 120 | 203 | 7209 | 12185 |
| 50 | 93 | 157 | 9307 | 15731 |

As can be seen from the values for the heat flow density, a significant heat flow can penetrate into the heat insulation body in the first seconds. The amounts of heat supplied will considerably influence the temperature course during the cooling down on account of the ability of the heat insulation body to store heat.

The simple model of a unilaterally "infinitely" expanded body can be taken to explain the basic relationships. This approximation is well satisfied in the case of the method of the invention since the brief heating processes limit the penetration of heat to one half the thickness of the heat insulation body. Simulation calculations with additional boundary conditions (heat transfer on the boundary surface, free convection during the cooling down) corroborate this. The heat flow through the surface of the test body during heating as constantly high should be considered a further boundary condition.

During the heating process the heat amount Q according to equation 6 is supplied to the body. Only the thermal penetration number b is valid as a variable parameter of equation 6 under reproducible test conditions ($\Delta\theta_o$; A; $\Delta t$ const.). The temperature field in the surface normal to the heat insulation body is described without consideration of the boundary surfaces by general differential equation 1. Given reproducible test conditions the temperature field in the interior of the heat insulation body is directly determined by the change of thermal diffusivity a.

In order to demonstrate changed characteristic values (thermal diffusivity and thermal penetration number) in heat insulation bodies a certain amount of heat is supplied in the test method to the formed insulation body over a defined time period. The heat flow through the surface determines the temperature course on the surface (localization of heat) thereby. As the calculation for the above table shows, the heat flow into the heat insulation body is inversely proportional to $\sqrt{\sqrt{t}}$ a constantly high surface temperature. As long as the boundary condition of the approximately constant heat flow from the heat source to the heat insulation body present under the test conditions is met, the surface. temperature must rise in a first approximation proportionally to $\sqrt{\sqrt{t}}$. Differences in the thermal penetration number b should therefore take effect in an inversely proportional manner on the achievable surface temperature at the end of the heating process, whereby a measuring criterion for deviations from the theoretical quality setting results.

In the method of the invention the cooling-off process of the surface is measured at free convection after the end of the heat supply. The course of these measured values can be described with a very good approximation by an exponential function of the type of equation $$\theta(t) = \theta_u + \theta_o \cdot exp(k \cdot t) \quad (7)$$

with the parameters $\theta_u$=lower boundary temperature at $t \to \infty$
$\theta_o$=temperature difference $\theta(t=0)-\theta''$ after heating to $\theta(t=0)$
$|k|$=cooling off constant.

These functional parameters are calculated from the course of the measured values and are dependent on the test conditions as well as on the properties of the heat insulation body. The amount of heat which penetrated into the heat insulation body essentially determines the temperature difference ($\theta_o$) whereas the cooling off constant $|k|$ and the lower boundary temperature ($\theta_u$) are also determined by the test construction and by the carrying out of the process.

Figure 4:
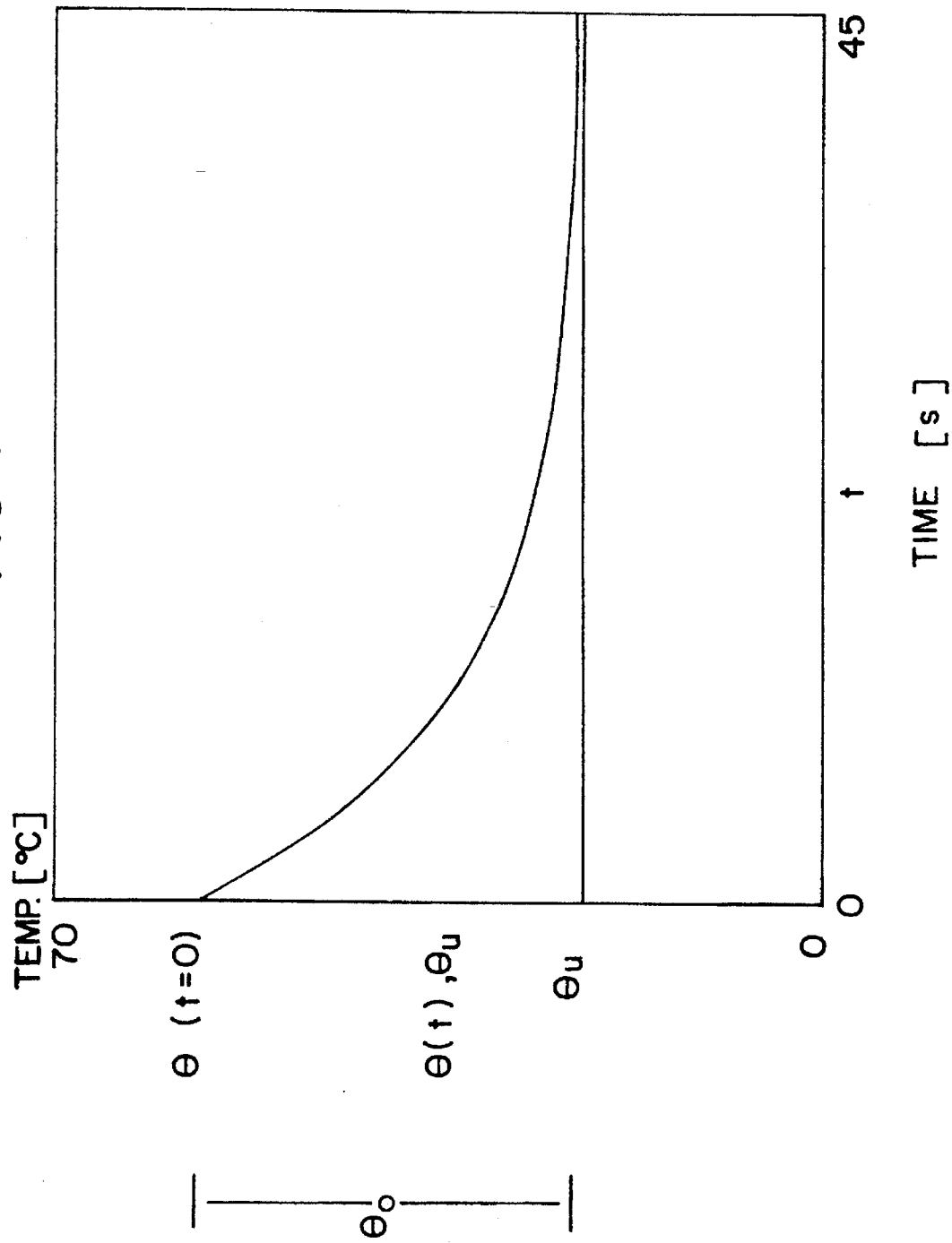
FIG. 4 is a plot of a cooling off curve.

The calculation of the cooling-off curves from measured data is presented in the following using an exemplary calculation. For this, a cooling-off curve is assumed which corresponds to the empirical values of practice (see also FIG. 4). The parameters required for this are:

| $\theta_u := 22°$ C. | ambient temperature |
|---|---|
| $\theta_o := 35°$ C. | temperature difference after heating |
| $k := -0.1$ | cooling-off constant |

Running or execution time of the cooling-off process, t, in seconds t:=0 to 45 s in steps to 0.1 s.

The measured temperature values of the cooling off which are necessary for calculating the curve parameters are at the times $t_1$ and $t_2$

| $t_1 := 1$ s | $t_2 := 20$ s | $\theta(t_1) = 53.669°$ C. |
|---|---|---|
| $\theta(t_2) = 26.737°$ C. | | |

The equations at these times are:

$$\theta(t_1) = \theta_u + \theta_o \, exp(|k|t_1) \quad (7.1)$$

$$\theta(t_2) = \theta_u + \theta_o \, exp(k \, t_2) \quad (7.2)$$

Equation (7.3) follows from the above via the difference (7.1–7.2)

$$\theta(t_1) - \theta(t_2) = \theta_o \{exp(k \, t_1) - exp(k \, t_2)\} \quad (7.3)$$

Cooling-off constant k can be calculated by dividing the two equations 7.1 and 7.2 (equation 7.4).

$$|k| = \frac{1}{t_1 - t_2} \ln \left[ \frac{\theta(t_1) - \theta_u}{\theta(t_2) - \theta_u} \right] \quad (7.4)$$

The heating temperature $\theta_o$ thus follows from 7.3.

$$\theta_o = \frac{\theta(t_1) - \theta(t_2)}{exp(k \cdot t_1) - exp(k \cdot t_2)} \quad (7.5)$$

According to the invention measurements are carried out with unsteady temperature conditions (heat flow in the heat insulation body not constant). In order to clarify the demonstrability and the magnitude of measured value changes dependent on the internal pressure, test measurements using thermography were carried out on 4 heat insulation bodies, two with less than 2 mbar internal pressure and two with about 70 mbar. In these measurements the heating of the heat insulation bodies took place by means of incandescent bulbs with a total output of 400 W. The construction stood free in the laboratory. The bulbs and the heat insulation body were held by stands. Differences in the surface temperatures of about 2° C. achievable by the heating could already be demonstrated between the heat insulation bodies with high internal pressure and those with low internal pressure with this simple construction.

An energy supply via thermal radiation has significant advantages over other methods which can be used. By means of adapting the wavelength range of the radiation source the energy supply can take place either directly onto the surface of the casing, which can optionally be a foil, or the greater part can pass through the casing onto the following shaping elements of the heat insulation bodies. Thus, the casing in the wavelength range of 3.5–6 μm used by way of example exhibits a transparency of more than 55%. The temperature distribution on the surface of the heat insulation body can be produced in a reproducible manner by means of a directed heat supply. As a result thereof, the non-determinable heat flows on the surface of the heat insulation body become approximately equal for each measurement and lose their influence on relative evaluations.

A thermal radiation source (called radiator in the following) supplies a relatively constant, reproducible heat flow for the time of the heating, which is necessary for the classification of the heat insulation bodies. The beginning and the time period of the heat supply can be very well defined by fading the radiator in and out.

The requirements of detecting the most precise temperatures possible with a high resolution in time without affecting the temperature field can only be satisfied in a contactless manner with a pyrometer adapted to the measuring conditions. A further important requirement for a precise temperature measurement is a well defined background radiation. This is achieved by choosing a material for the inner surfaces of the housing of the measuring device which reflects the thermal radiation from the heated specimen surface almost quantitatively. During the measuring time, the heat flux of the heating source is thereby directed towards a water cooled surface which absorbs more than 98% of the arriving thermal radiation. For the surface measuring (that is, on the casing) a wavelength range of 7–20 μm can be selected in which the characteristic radiation of the foil is more than 90%.

The radiator directed during the heating-up phase onto the surface of the test specimen must be brought into a position during the subsequent measuring in which position it is turned away from the measured area and does not affect the measuring process. The position of the pyrometer during the measuring is given by the physical boundary conditions (diameter of measured spot, angle of radiation, temperature field). Optimum conditions result when the pyrometer assumes the position of the radiator, that is, vertical to the surface. The switching process between heating and measuring should take place as rapidly as possible and not load the devices. A fixing is necessary at each switching process in order to assure a sufficiently precise reproduction of the measuring position. A simple operation is to be aimed at for manual operation. The above-mentioned conditions are largely satisfied by mounting the radiator and the pyrometer, offset by 90° relative to one another, on a rotatable shaft with adjustable stop location.

Figure 2:
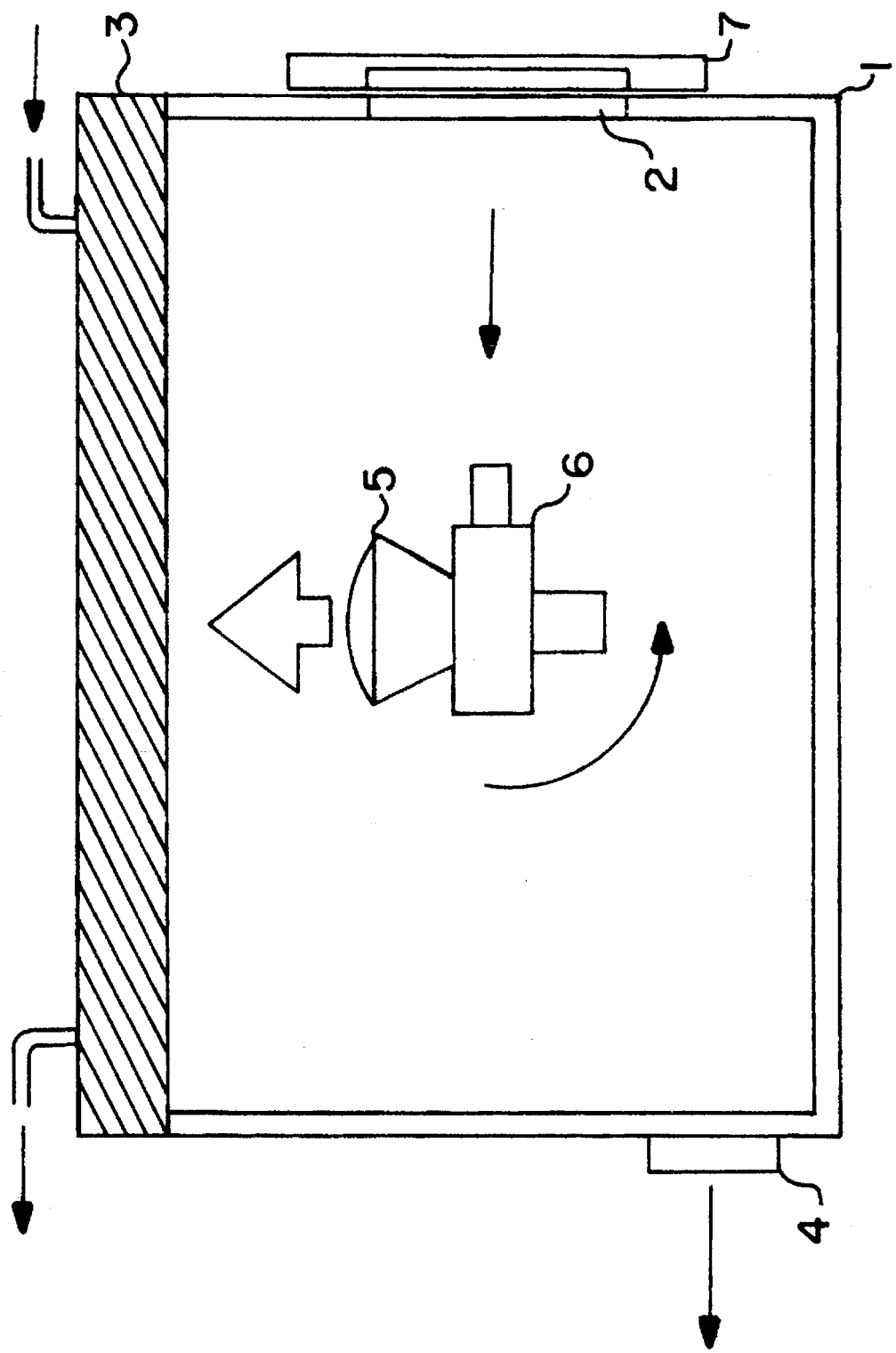
FIG. 2 is a schematic cross-section of the apparatus of FIG. 1 with the pyrometer rotated 90° C.

A device which is schematically shown in FIGS. 1 and 2 can be used to carry out the determination of the thermal relaxation.

According to FIG. 1 housing 1 is provided on one side with window 2, on its upper side with cooling means 3 controlled with cooling water and with ventilation opening 4. Radiator 5 and the temperature measurement means pyrometer 6 which measures the thermal radiation output, which are arranged vertically to one another and can rotate as a fixed unit, are located in the housing. Heat insulation panel 7 is placed up to the outside of window 2 before the measurement. A defined amount of heat is supplied by irradiation by radiator 5 and the defined opening of window 2 to heat insulation body 7 over a determined time period. After the irradiation, the heating means radiator 5, is immediately rotated with pyrometer through 90° so that pyrometer 6 can measure the thermal radiation output as shown in FIG. 2. The testing of the heat insulation body takes place in that a computer (not shown) compares the calculated values of $|k|$ and $\theta_o$ from the cooling off curve with a standard.

The testing of a heat insulation body such as a panel in accordance with the invention can be carried out in detail as follows, at which time the following technical conditions are observed:

The measuring signal of the pyrometer is read into a computer (PC) via an analog/digital converter card. The representation of the measured values, the documentation and the evaluation take place via the program.

| Pyrometer: | Wavelength range: | 8–20 gm |
| --- | --- | --- |
| | Diameter of measured spot: | 20 ± 5 mm |
| | Resolution in time: | 100 ms |
| | Temperature resolution: | 0.2° C. |
| | Output signal: | 0–20 mA at 0–100° C. |
| A/D converter: | Resolution | 12 bit |
| | Channel number: | 16 |
| | Converter rate: | <1 ms |
| Radiator: | Output: | 60 W |
| | Temperature: | 320 ± 60° C. |
| | Degree of emission: | 98% |
| | $\lambda_{max}$: | 4.87 μm |
| System data: | Air heating 1) (60 watts): | 2.0° C. |
| | Background radiation (60 watts): | 18 ± 2° C. |
| | Preheating time: | 30 minutes |

1) measured at vertical orientation of the measuring window in a stationary state.

Based on this information a person skilled in the art could prepare a suitable program and computer operation to carry out the invention.

The test system should be switched on at least 30 minutes before the first test. For this the water supply of cooling surface 3 must first be opened. Then the current supply for pyrometer 6, radiator 5 and ventilator 4 is cut in. After an operating time of 30 minutes the test system is so stable thermally that the tests can be started. The measuring computer is to be put in operation and the testing program started for the computer-supported testing.

The temperature in the measuring space is measured with pyrometer 6 before the installation of the heat insulation body. For this, radiator 5 must be aligned with the open window. The pyrometer is subsequently aligned with the free window. The heat insulation body can now be brought in front of the window. The measuring of the initial temperature of the heat insulation body follows. Radiator 5 is then aligned with the surface of the heat insulation body. The heating process begins. After 45 seconds pyrometer 6 is again pivoted onto the surface of the heat insulation body and the temperature course measured for approximately 50 seconds. The testing procedure is ended thereafter and the heat insulation body can be removed. In the computer-supported testing the evaluation takes place automatically at the end of the test.

Starting from the already described iteration method, three evaluation magnitudes can be defined which, when viewed in a comparison, permit an evaluation of the quality of the test specimen. These magnitudes are:

| 1. | Amount of the exponent $|k|$ | (too great an amount = reject) |
| --- | --- | --- |
| 2. | Heating $\Delta\theta_1$ | (too little heating = reject) |
| 3. | Cooling off $\Delta\theta_2$ | (too little cooling off = reject) | and are defined by the iteration equation as follows:

$$|k| = \frac{1}{t} \ln \frac{\theta(t) - \theta_u}{\theta_o}$$

$t$ = time
$\theta(t = 0)$ = highest temp. of the heat insulation body $\Delta\theta_1 = \theta(t = 0) - \theta_{before}$ $\theta_{before}$ = temperature before warming $\Delta\theta_2 = \theta(t = 0) - \theta(t = \infty)$ $\theta(t = \infty)$ = Temperature to which the heat insulation body cools off.

For the calibration of the test system five good reference specimens proven by other absolute test methods are to be measured at least 4 times. Reference specimens are defined by a certain maximum value of their thermal conductivity coefficient, their internal pressure, and their moisture content, determined by this absolute test methods after the calibration of the test system. The tolerance range for the testing is the value range of the maximum absolute error formed from these 20 measurements of the reference specimens (DIN 1319, B1.3), which is related to a confidence range of 99%. The upper boundary value of the heating ($\Delta\theta_1$ max.) follows from the greatest value of the heating range and the lower boundary value of the heating ($\Delta\theta_1$ min.) follows from the smallest value of the heating range.

The other boundary value definitions are determined in the same manner. The following thus result:

1. $\Delta\theta_{1(max/min)}$ upper/lower boundary value of the heating
2. $\Delta\theta_{2(max/min)}$ upper/lower boundary value of the cooling off.
3. $|k|_{(max/min)}$ upper/lower boundary value for the amount of the exponent.

In order to evaluate the carrying out of the test the combined value from heating and exponent can be used in the described configuration of the test location. The distinction of instance is cited in the following.

Measured values of the test specimen:

$\Delta\theta_{1(p)}$; $\Delta\theta_{2(p)}$; $|k|_{(p)}$

| 1st instance | |
| --- | --- |
| Result of the measuring: | $\Delta\theta_{1(max)} > \Delta\theta_{1(p)} > \Delta\theta_{1(min)}$ |
| | $\Delta\theta_{2(max)} > \Delta\theta_{2(p)} > \Delta\theta_{2(min)}$ |
| | $|k|_{(max)} > |k|_{(p)} < |k|_{(min)}$ |

It follows therefrom that the heat insulation body is within the specification.

2nd instance

Result of the measuring:
$$\Delta\theta_{1(max)} < \Delta\theta_{1(p)}$$
$$\Delta\theta_{2(max)} < \Delta\theta_{2(p)}$$
$$|k|_{(max)} > |k|_{(p)} < |k|_{(min)}$$

It follows therefrom that the heat insulation body is probably within the specification but was heated too long for a reliable evaluation. The measuring is invalid and must be repeated.

3d instance

Result of the measuring:
$$\Delta\theta_{1(p)} < \Delta\theta_{1(min)}$$
$$\Delta\theta_{2(p)} < \Delta\theta_{2(min)}$$

It follows therefrom that this heat insulation body is clearly outside of the desired specification.

Figure 3:
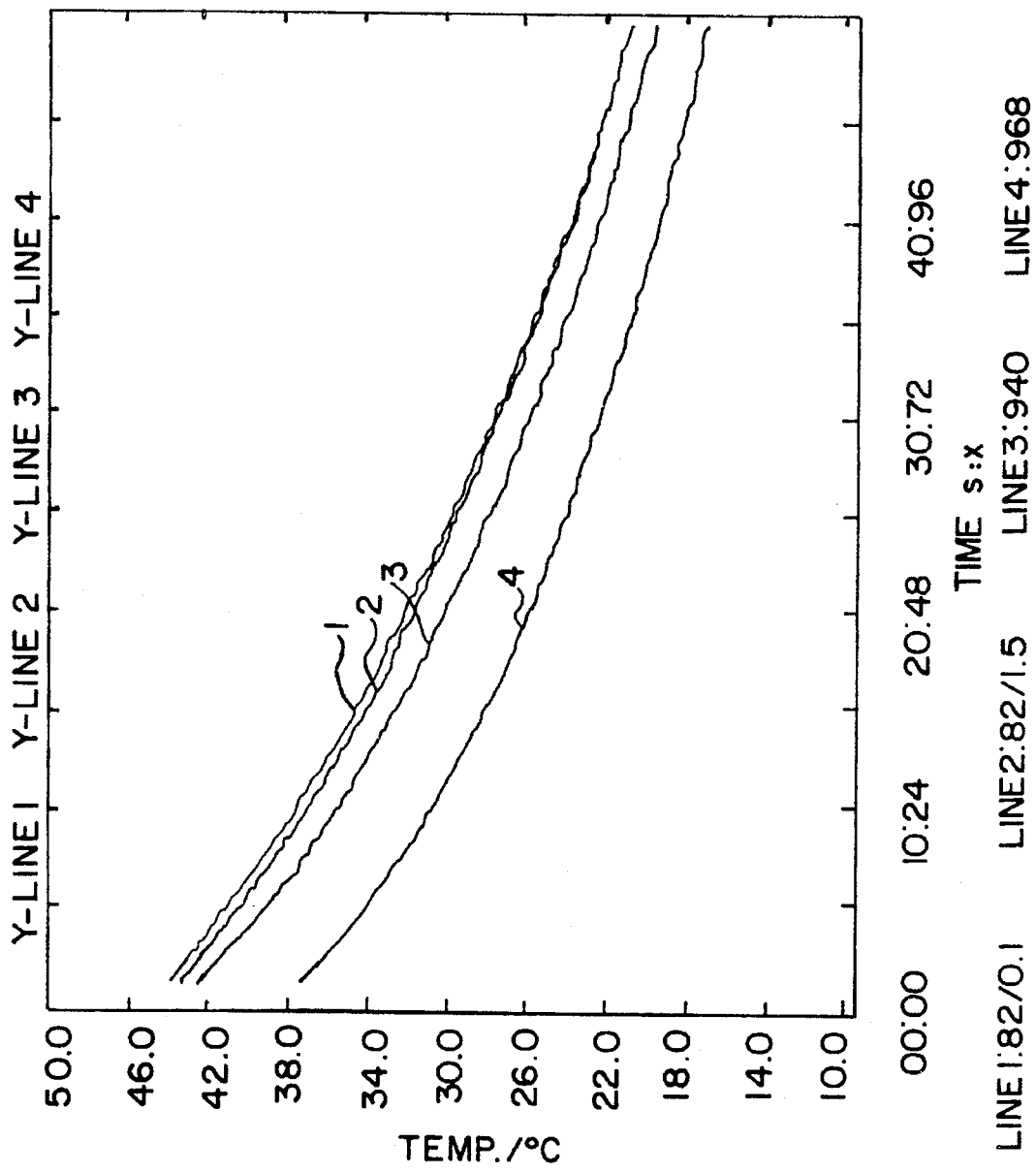
FIG. 3 is a graph of the test results obtained in accordance with the present invention.

Test measurements are presented in the following which correspond to described instances 1 and 3. Measuring records 1 and 2 of heat insulation bodies 82/0.1 and 82/1.5 exhibit data which is achieved by error-free heat insulation bodies. Heat insulation bodies with a relative moisture of 0% and with an internal pressure less than 10 mbar are considered to be error-free. The data for the relative moisture and the internal pressure was determined indirectly in the case of these heat insulation bodies by destructive testing. The measuring records 3 and 4 of heat insulation bodies 940 and 968 show which results are yielded by heat insulation bodies with slight moisture (2–6%) and an internal pressure of approximately 4–10 mbar. A test record for these 4 heat insulation bodies follows below. The graphic evaluation of this measuring is shown in FIG. 3.

1)

| | |
|---|---|
| Data file: | F:\VERGLEIC\PANELX01.DAT |
| Panel designation: | 82/0.1 |
| Charge designation: | 1 |
| Date: | 5-18-93 |
| Time: | 09:52 |
| Measuring location: | Test layout |
| Sensor: | HEIM.KT15 |
| Tester: | Elke Berlemann |
| Commentary: | Internal pressure of the panel: <3 mbar |

Test conditions

| | |
|---|---|
| Ambient temperature: | 20.9° C. |
| Initial temperature: | 23.4° C. |

Calculated values

| | |
|---|---|
| Heated by: | 43.2° C. |
| Cooled off by: | 37.0° C. |
| Exponent: | −2.017E-02 |
| Absolute deviation: | 9.898E-03° C. |
| Evaluation: | Error-free |

2)

| | |
|---|---|
| Data file: | F:\VERGLEIC\PANELX02.DAT |
| Panel designation: | 82/1.5 |
| Charge designation: | 1 |
| Date: | 5-18-93 |
| Time: | 10:27 |
| Measuring location: | Test layout |
| Sensor: | HEIM.KT15 |
| Tester: | Elke Berlemann |
| Commentary: | Internal pressure of the panel: <5 mbar |

Test conditions

| | |
|---|---|
| Ambient temperature: | 21.5° C. |
| Initial temperature: | 23.7° C. |

Calculated values

| | |
|---|---|
| Heated by: | 42.7° C. |
| Cooled off by: | 35.6° C. |
| Exponent: | −2.083E-02 |
| Absolute deviation: | 9.025E-02° C. |
| Evaluation: | Error-free |

3)

| | |
|---|---|
| Data file: | F:\VERGLEIC\PANELX03.DAT |
| Panel designation: | 940 |
| Charge designation: | 9 |
| Date: | 3-3-93 |
| Time: | 09:39 |
| Measuring location: | Test layout |
| Sensor: | HEIM.KT15 |
| Tester: | Elke Berlemann |

| | | |
|---|---|---|
| Commentary: | Internal pressure about 4 mbar, moisture 2% | |
| Test conditions | | |
| Ambient temperature: | 21.0° C. | |
| Initial temperature: | 22.1° C. | |
| Calculated values | | |
| Heated by: | 42.3° C. | |
| Cooled off by: | 32.8° C. | |
| Exponent: | −2.448E-02 | |
| Absolute deviation: | 6.271E-02° C. | |
| Evaluation: | reject | |
| 4) | | |
| Data file: | F:\VERGLEIC\PANELX04.DAT | |
| Panel designation: | 968 | |
| Charge designation: | 10 | |
| Date: | 3-3-93 | |
| Time: | 10:43 | |
| Measuring location: | Test layout | |
| Sensor: | HEIM.KT15 | |
| Tester: | Elke Berlemann | |
| Commentary: | Internal pressure about 11 mbar, moisture 6% | |
| Test condition | | |
| Ambient temperature: | 21.3° C. | |
| Initial temperature: | 22.5° C. | |
| Calculated values | | |
| Heated by: | 37.1° C. | |
| Cooled off by: | 27.1° C. | |
| Exponent: | −2.845E-02 | |
| Absolute deviation: | 1.193E-01° C. | |
| Evaluation: | reject | |
| Record of the test specimens which are not within the desired specification or in the case of which there is an erroneous measurement. | | |
| Tolerance ranges of the specification: | | |
| Heating: | 42.4–43.3° C. | |
| Cooling off: | 34.5–35.5° C. | |
| Exponent amount: | 2.07E-02–2.14E-02 | |
| Measurements from: | 5-18-93 to 3-3-93 | |
| Measuring location: | Test layout | |
| Sensor: | HEIM.KT15 | |
| Specimen number: | 4, rejects therein: 2 | |
| Test specimens: | 82/0.1, 82/1.5, 940, 968 | |

| Spec. | Date | Designat. | Ambient | Initial | Heating | Cooling Off | Exponent |
|---|---|---|---|---|---|---|---|
| Reject | 3-3-93 | 940 | 21.0 | 22.1 | 42.3 | 32.8 | −2.45E-02 |
| Reject | 3-3-93 | 968 | 21.3 | 22.5 | 37.1 | 27.1 | −2.84E-02 |

In carrying out the invention, a flat panel or other shaped body of insulation is subjected to a source of constant elevated temperature at a direction normal to the surface of the body, for a determined period of time. After heating, contactless temperature measurement means measure thermal radiation output from the insulation body, then the data obtained by contactless temperature measurement means is used by computer or calculator means to calculate the parameters $$b_1 = \sqrt{\sqrt{\lambda \rho C}} = 38.88 \, J \cdot m^{-2} \cdot K^{-1} \cdot s^{1/2}$$

which are compared with given parameters.

The calculation is carried out as follows with the measured temperature values of the cooling off of the insulation body which are necessary for calculating the curve parameters at the time $t_1$ and $t_2$.

$$\theta(t_1) = \theta_u + \theta_o exp(kt_1)$$

$$\theta(t_2) = \theta_u + \theta_o exp(kt_2)$$

$$\theta(t_1) - \theta(t_2) = \theta_o \{exp(kt_1) - exp(kt_2)\}$$

The cooling off constant k can be calculated by dividing the above equations thusly $$\theta(t_1) = \theta_u + \theta_o \exp(kt_1) \div \theta(t_2) = \theta_u + \theta_o \exp(kt_2)$$

$$|k| = \frac{1}{t_1 - t_2} \ln \left[ \frac{\theta(t_1) - \theta_u}{\theta(t_2) - \theta_u} \right]$$

Then the heating temperature can be calculated:

$$\theta_o = \frac{\theta(t_1) - \theta(t_2)}{\exp(k \cdot t_1) - \exp(k \cdot t_2)} \tag{7.5}$$

The automatic acquisition of measured values with subsequent evaluation of the data takes place with a data-processing program. For the documentation and ongoing statistical research the measuring parameters, measured values and the computational values of each individual measurement are retained in data files on a storage medium accessible to the computer. The evaluation can be outputted with any printer. The program is designed so that it is easy to operate after a brief introduction.

The calculation of the cooling-off curve according to equation 7 takes place from the given data of the measurement as follows:

| Measured values: | o | n-measured values (n > 100) |
|---|---|---|
| | o | initial temperature |
| | o | time between two measurements |

The values to be calculated are:

| | |
|---|---|
| o | temperature after the heating ($\theta_o$) |
| o | exponent of the function (k) |
| o | damping temperature ($\theta_u$). |

FIG. 5 illustrates the iteration process. Only the non-shaded part of the entire curve course is known. The functional parameters are calculated as described in the following with the setting of a time range $\Delta t$:

1. The initial temperature is $\theta_u$.
2. The calculation of $|k|$ and $\theta_o$ from the values for $\theta(t_1)$ and $\theta(t_2)$ with $t_2-t_1=\Delta t$ (see exemplary calculation above).
3. m-fold repetition of point 2.
4. The formation of the mean average value from the m-values for $|k|$ and $\theta_o$.
5. The monitoring of the deviation of the individual values for $|k|$; optionally eliminate outliers from the average value.
6. The calculation of the curve according to equation 7.
7. The calculation of the deviation of the curve course.
8. If the boundary value of the deviation has been exceeded a changing of the set parameter $\theta_u$ follows and the operating sequence begins again at point 2. Otherwise, the calculation is accepted.

Further variations and modifications will become apparent to those skilled in the art from the foregoing and are intended to be encompassed by the claims appended hereto.

German prior application P 43 37 840.4 is relied on and incorporated herein by reference.

We claim:

1. A method of testing heat insulation shaped bodies for purposes of evaluation comprising placing a shaped heat insulation body having a surface in a measuring space, measuring the initial temperature of said heat insulation body under ambient conditions prior to heating;

subjecting said shaped heat insulation body to thermal radiation for contactless heating of said surface for a sufficient period of time to heat at least said surface of said body to an elevated temperature;

removing said radiation from said body and measuring the initial temperature decrease of the surface with a contactless temperature measurement means to obtain a temperature/time profile of said surface; calculating the thermal conduction coefficient $|k|$ as follows:

$$|k| = \frac{1}{t} \ln \frac{\theta(t) - \theta_u}{\theta_o}$$

and comparing $|k|$ with a standard thermal conduction coefficient, wherein (t) is time, $\theta_o$ is the temperature of the surface of said body after heating, $\theta_u$ is the temperature of the surroundings, and $\theta(t)$ the surface temperature at time (t), whereby said heat insulation shaped body is evaluated.

* * * * *